(12) United States Patent
Nimgaonkar et al.

(10) Patent No.: US 10,994,107 B2
(45) Date of Patent: May 4, 2021

(54) IMPLANTABLE BODY-DRIVEN SHUNT PUMP (71) Applicant: The Johns Hopkins University, Baltimore, MD (US)

(72) Inventors: Ashish Nimgaonkar, Ellicott City, MD (US); Matthew Petney, Albuquerque, NM (US); Kevin James Colbert, Baltimore, MD (US); Laura Scavo, Bethesda, MD (US); Michelle Camacho, Rockville, MD (US)

(73) Assignee: The Johns Hopkins University, Baltimore, MD (US)

( * ) Notice: Subject to any disclaimer, the term of this patent is extended or adjusted under 35 U.S.C. 154(b) by 295 days.

(21) Appl. No.: 15/532,910

(22) PCT Filed: Dec. 7, 2015

(86) PCT No.: PCT/US2015/064319
§ 371 (c)(1),
(2) Date: Jun. 2, 2017

(87) PCT Pub. No.: WO2016/090378
PCT Pub. Date: Jun. 9, 2016

(65) Prior Publication Data
US 2017/0361074 A1 Dec. 21, 2017

Related U.S. Application Data (60) Provisional application No. 62/088,390, filed on Dec. 5, 2014.

(51) Int. Cl.
A61M 27/00 (2006.01)
A61M 1/00 (2006.01)
(Continued)

(52) U.S. Cl.
CPC ........ *A61M 27/002* (2013.01); *A61M 1/0066* (2013.01); *A61M 25/0075* (2013.01);
(Continued)

(58) Field of Classification Search
CPC ................... A61M 27/002; A61M 2202/0401
See application file for complete search history.

(56) References Cited

U.S. PATENT DOCUMENTS 4,657,530 A * 4/1987 Buchwald ............. A61M 1/008
604/247
5,607,418 A * 3/1997 Arzbaecher ....... A61M 5/16877
604/891.1
(Continued)

FOREIGN PATENT DOCUMENTS

EP 0270205 A2 6/1988

OTHER PUBLICATIONS

De Waele et al, "Intra-abdominal Hypertension and Abdominal Compartment Syndrome," Am. J. Kidney Dis., 57(1): 159-69 (2011).
(Continued)

*Primary Examiner* — Leslie R Deak
(74) *Attorney, Agent, or Firm* — Venable LLP; Henry J. Daley; Aziz H. Poonawalla (57) ABSTRACT An implantable, body-driven shunt pump includes a pump body defining a fluid inlet, a fluid outlet and a fluid chamber therebetween; an inlet valve arranged in the fluid inlet, the inlet valve being a one-way valve arranged such that it is operable to allow fluid flow into the fluid chamber and to prevent fluid flow out of the fluid chamber; and an outlet valve arranged in the fluid outlet, the outlet valve being a one-way valve arranged such that it is operable to allow fluid flow out of the fluid chamber and to prevent fluid flow into the fluid chamber. The pump body includes an expandable and contractible component in a portion of the pump body
(Continued)

that defines the fluid chamber such that the fluid chamber changes volume in response to a change in pressure of fluid in the fluid chamber.

19 Claims, 9 Drawing Sheets

(51) Int. Cl.
*A61M 25/00* (2006.01)
*A61M 60/268* (2021.01)
*A61M 60/882* (2021.01)

(52) U.S. Cl.
CPC ......... *A61M 60/268* (2021.01); *A61M 60/882* (2021.01); *A61M 2025/0078* (2013.01); *A61M 2202/0401* (2013.01)

(56) References Cited

U.S. PATENT DOCUMENTS

| | | | | |
|---|---|---|---|---|
| 5,830,172 | A * | 11/1998 | Leveen | A61M 27/006 604/9 |
| 6,682,500 | B2 * | 1/2004 | Soltanpour | A61F 9/00781 604/521 |
| 8,394,048 | B2 | 3/2013 | Burnett | |
| 8,771,221 | B2 | 7/2014 | Burnett | |
| 9,370,422 | B2 * | 6/2016 | Wang | A61F 2/2436 |
| 9,603,742 | B2 * | 3/2017 | Sanchez | A61F 9/00781 |
| 2010/0031263 | A1 | 2/2010 | Lamothe | |

OTHER PUBLICATIONS

Fleming et al., "Incidence of cirrhosis in the UK: a population-based study," Conference Abstract, British Association for the Study of Liver Disease, ASM (2007).
Ginès et al., "Paracentesis with intravenous infusion of albumin as compared with peritoneovenous shunting in cirrhosis with refractory ascites," N. Engl. J. Med. 325(12):829 (1991).
Organ Procurement and Transplantation Network: http://optn.transplant.hrsa.gov/.
Rössle and Gerbes, "TIPS for the treatment of refractory ascites, hepatorenal syndrome and hepatic hydrothorax: a critical update," Gut, 59 (7): 988-1000 (2010).
Saab et al., "TIPS versus paracentesis for cirrhotic patients with refractory ascites," (S. Saab, Ed.). Chichester, UK: John Wiley & Sons, Ltd. (1996).
Salerno et al, "Refractory ascites: pathogenesis, definition and therapy of a severe complication in patients with cirrhosis," Liver Int., 30 (7): 937-47 (2010).
Sort et al, "Effect of IV Albumin on Renal Impairment and Mortality in Patients with Cirrhosis and SBP," NEJM, 341(6): 403-9 (1999).
"WGO Practice Guideline: Condition: Management of Ascites Complicating Cirrhosis in Adults," http://www.worldgastroenterology.org/assets/downloads/en/pdf/guidelines/14_management_ascites_en.pdf. (7 pages).
White et al., "Denver peritoneovenous shunts for the management of malignant ascites: a review of the literature in the post LeVeen Era," The American Surgeon, 77(8), 1070-1075 (2011).
International Search Report and Written Opinion in International Application No. PCT/US2015/064319, dated Mar. 21, 2016.

* cited by examiner

BOTTOM OF MOLD LID

FIG. 8A

TOP OF MOLD LID

FIG. 8B

BASE OF MOLD

INLET/OUTLET BOTTOM OF MOLD LID

FIG. 9A

INLET/OUTLET TOP OF MOLD LID

FIG. 9B

INLET/OUTLET MOLD BASE

FIG. 9C

AIR CHAMBER MOLD BASE

FIG. 9D

AIR CHAMBER BOTTOM OF MOLD LID

FIG. 9E

AIR CHAMBER TOP OF MOLD LID

IMPLANTABLE BODY-DRIVEN SHUNT PUMP

This application is a U.S. National Phase Application of PCT/US2015/064319, filed on Dec. 7, 2015, which claims priority to U.S. Provisional Application No. 62/088,390 filed on Dec. 5, 2014, the entire contents of which are hereby incorporated by reference.

This invention was made with government support under grant number TR001079 awarded by the National Institutes of Health. The government has certain rights in this invention.

BACKGROUND

1. Field of Invention

The field of the currently claimed embodiments of this invention relates to shunt pumps, and more particularly to implantable, body-driven shunt pumps.

2. Discussion of Related Art

Ascites is a condition where fluid accumulates in the peritoneal cavity of the abdomen.[1] It most commonly affects patients with cirrhosis of the liver (in 75% of all cases). Cirrhotic ascites can be managed in its early stages with dietary salt restriction and diuretic medications. However, these patients eventually become refractory to medical therapy. Diuretic-induced renal impairment occurs in 20% of cirrhotic patients treated with diuretics even before these patients are labeled as diuretic resistant[1]. About 5%-10% of patients with ascites develop refractory ascites at which point, their two-year probability of survival is less than 30%.[1] The only definitive treatment at this stage is liver transplantation, which is limited due to the availability of donor organs (6,300 liver transplants were performed in US in 2010).[2] The practice of using peritoneovenous shunting (e.g., Denver shunt) has mostly been abandoned due to its complication rates, particularly related to infusion of peritoneal fluid into the vascular space (DIC, Variceal bleeding).[3] Transjugular intrahepatic portosystemic shunt (TIPS) is being advocated for management of refractory ascites but is only done in a limited number of patients and carry the risk of exacerbating hepatic encephalopathy.[4,5] Therefore no effective treatment options currently exist for this patient population.

Patients with refractory ascites experience considerable abdominal discomfort and difficulty breathing leading to significant morbidity. In extreme cases, the increased intra-abdominal pressure can cause chronic abdominal compartment syndrome, compromising blood supply to abdominal organs such as kidneys.[6] The recurrent symptoms in these patients are alleviated by directly draining 5 L-10 L of fluid in large volume paracentesis (LVP) on an average every 2-4 weeks and suffer from deteriorating symptoms in the interim as the fluid re-accumulates.[7] Furthermore, LVP is typically followed by administration of intravenous albumin due to the significant risk of kidney damage associated with it (6 g-8 g of albumin per liter of fluid removed). With intravenous albumin costing up to $25/g, the total cost of each patient visit for LVP is estimated at $3000.[8,9] Together, these frequent interventions present a substantial cost burden to the healthcare system, not to mention the significant deterioration in the quality of the life these patients. There thus remains a need for improved devices and methods for treating refractory ascites.

SUMMARY

An implantable, body-driven shunt pump according to some embodiments of the current invention includes a pump body defining a fluid inlet, a fluid outlet and a fluid chamber therebetween; an inlet valve arranged in the fluid inlet, the inlet valve being a one-way valve arranged such that it is operable to allow fluid flow into the fluid chamber and to prevent fluid flow out of the fluid chamber; and an outlet valve arranged in the fluid outlet, the outlet valve being a one-way valve arranged such that it is operable to allow fluid flow out of the fluid chamber and to prevent fluid flow into the fluid chamber. The pump body includes an expandable and contractible component in a portion of the pump body that defines the fluid chamber such that the fluid chamber changes volume in response to a change in pressure of fluid in the fluid chamber.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Accordingly, some embodiments of the current invention are directed to a new shunt pump that provides a new approach of peritoneogastric shunting to allow management of patients at home in order to improve their quality of life and reduce cost of care.

Figure 1:
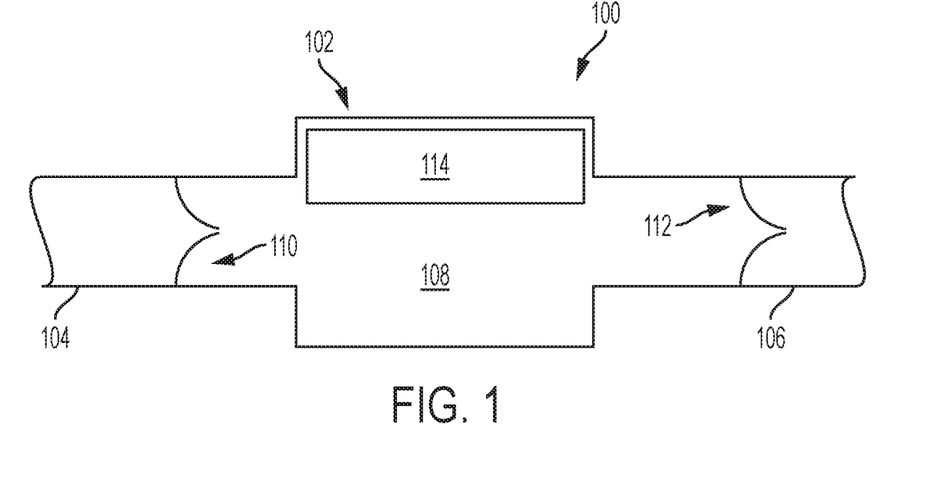
FIG. 1 is a schematic illustration of an implantable, body-driven shunt pump according to an embodiment of the current invention.

FIG. 1 is a schematic illustration of an implantable, body-driven shunt pump 100 according to an embodiment of the current invention. The implantable, body-driven shunt pump 100 includes a pump body 102 defining a fluid inlet 104, a fluid outlet 106 and a fluid chamber 108 therebetween. The implantable, body-driven shunt pump 100 also includes an inlet valve 110 arranged in the fluid inlet 104. The inlet valve 110 is a one-way valve arranged such that it is operable to allow fluid flow into the fluid chamber 108 and to prevent fluid flow out of the fluid chamber 108. The implantable, body-driven shunt pump 100 also includes an outlet valve 112 arranged in the fluid outlet 106. The outlet valve 112 is a one-way valve arranged such that it is operable to allow fluid flow out of the fluid chamber 108 and to prevent fluid flow into the fluid chamber 108. The pump body 102 includes an expandable and contractible component 114 in a portion of the pump body 102 that defines said fluid chamber 108 such that the fluid chamber 108 changes volume in response to a change in pressure of fluid in the fluid chamber 108.

In some embodiments, the pump body 102, the inlet valve 110, and the outlet valve 112 are all biocompatible materials. In some embodiments, the implantable, body-driven shunt pump 100 has a size suitable to be implantable into an abdominal cavity of a patient. In other applications, the implantable, body-driven shunt pump 100 be placed in the abdominal wall superficial to the abdominal muscles, or can be left outside the body. However, the general concepts of the current invention are not limited to only this application. For example, the implantable, body-driven shunt pump 100 can have a size suitable to be implantable into other parts of the body, such as, but not limited to, the eye for treating glaucoma, pleural effusion, hydrocephalus, etc. In some embodiments, the fluid inlet 104 is configured to be arranged in a peritoneal cavity of the patient, and the fluid outlet 106 is configured to be arranged in at least one of the stomach or the urinary bladder of the patient while the fluid inlet 104 is arranged in the peritoneal cavity so as to pump fluid from the peritoneal cavity into the stomach or the urinary bladder in response to changes in volume of the fluid chamber 108.

In some embodiments, the pump body 102 can include an insert of a compressible material as part of a section thereof defining the fluid chamber 108. In other words, the expandable and contractible component 114 can be, or can include, a compressible material. The insert can be selected from elastic materials, for example, according to the particular application. Closed cell foam and/or many small gas filled collapsible pellets are a couple examples of materials that can be used for inserts in some embodiments. However, the general concepts of the current invention are not limited to those particular materials.

In some embodiments, the pump body 102 defines a compressible compartment as part of a section the pump body 102 that defines the fluid chamber 108. In some embodiments, the compressible compartment can include a thin membrane separating the fluid chamber from the interior and any material within the compressible compartment. In some embodiments in which there is a compressible compartment, the shunt pump also includes a compressible fluid contained within the compressible compartment. In some embodiments, the compressible fluid can be a gas having a preselected composition and pressure at a selected temperature prior to use. In other words, the implantable, body-driven shunt pump 100 can be manufactured and supplied with such a gas having the preselected composition and pressure. One should understand that the pressure of such a gas enclosed in the compressible compartment changes with temperature, as well as by applied pressures during use.

In some embodiments, the pump body 102 has a substantially rigid outer surface in a section defining the fluid chamber 108. In some embodiments, the fluid inlet 104 forms and/or can include an inlet tube and the fluid outlet 106 forms and/or can include an outlet tube. In some embodiments, at least one of the inlet tube and the outlet tube can define a plurality of holes along a portion of an axial length thereof. In some embodiments, at least one of the inlet tube and the outlet tube can be coated with an antibacterial agent. In some embodiments, at least one of the inlet tube and the outlet tube can be coated with an anti-coagulant. In some embodiments, the pump body 102 can be made at least partially from silicone. In some embodiments, the pump body 102 is formed with a silicone base to curing ratio of between 5:1 to 100:1. In some embodiments, the pump body 102 is formed with a silicone base to curing ratio of between 10:1 to 50:1. In some embodiments, the pump body 102 is formed with a silicone base to curing ratio of between 10:1 to 40:1. In some embodiments, the pump body 102 is formed with a silicone base to curing ratio of about 20:1.

In some embodiments, the pump body 102 defines a rigid chamber, within which is an expandable and contractible component. This component can be filled with fluid, gas, multiple small pellets etc. and separated from the fluid flow by a membrane.

In some embodiments, the pump body 102 defines a semi-rigid chamber, within which is an expandable and contractible component. This component can be filled with fluid, gas, multiple small pellets etc. and separated from the fluid flow by a membrane.

In some embodiments, the pump body 102 can have at least a section that is at least partially flexible to be responsive to external forces on the pump body 102 in addition to differential pressures at the inlets and outlets.

Figure 2:
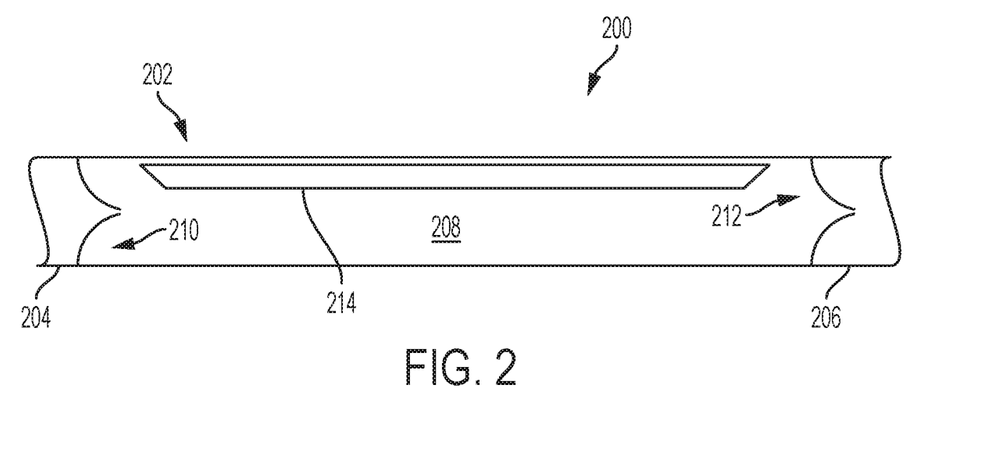
FIG. 2 is a schematic illustration of an implantable, body-driven shunt pump according to another embodiment of the current invention.

FIG. 2 is a schematic illustration of an implantable, body-driven shunt pump 200 according to another embodiment of the current invention. This embodiment can is similar to the embodiment of FIG. 1, but is tubular in structure. The implantable, body-driven shunt pump 200 includes a pump body 202 defining a fluid inlet 204, a fluid outlet 206 and a fluid chamber 208 therebetween. The implantable, body-driven shunt pump 200 also includes an inlet valve 210 arranged in the fluid inlet 204. The inlet valve 210 is a one-way valve arranged such that it is operable to allow fluid flow into the fluid chamber 208 and to prevent fluid flow out of the fluid chamber 208. The implantable, body-driven shunt pump 200 also includes an outlet valve 212 arranged in the fluid outlet 206. The outlet valve 212 is a one-way valve arranged such that it is operable to allow fluid flow out of the fluid chamber 208 and to prevent fluid flow into the fluid chamber 208. The pump body 202 includes an expandable and contractible component 214 in a portion of the pump body 202 that defines said fluid chamber 208 such that the fluid chamber 208 changes volume in response to a change in pressure of fluid in the fluid chamber 208.

Figure 3A:
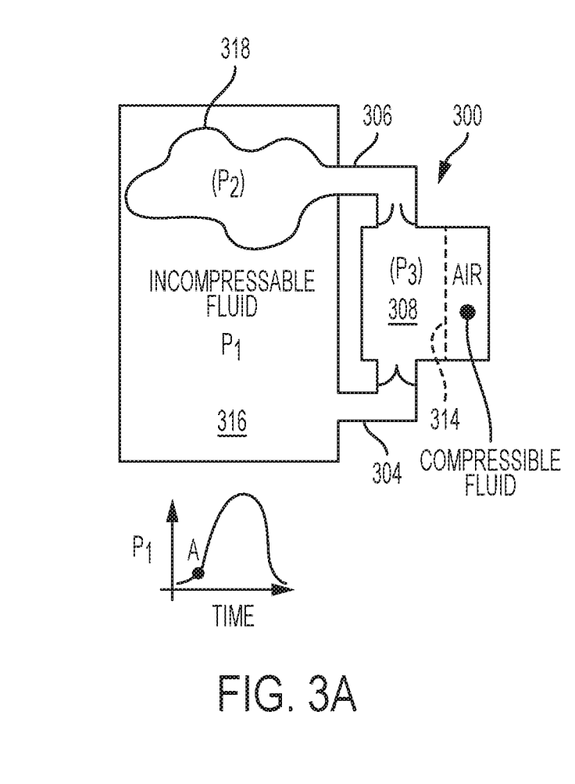
FIGS. 3A-3C provide schematic illustrations to help explain the operation of an implantable, body-driven shunt pump according to an embodiment of the current invention.
Figure 3B:
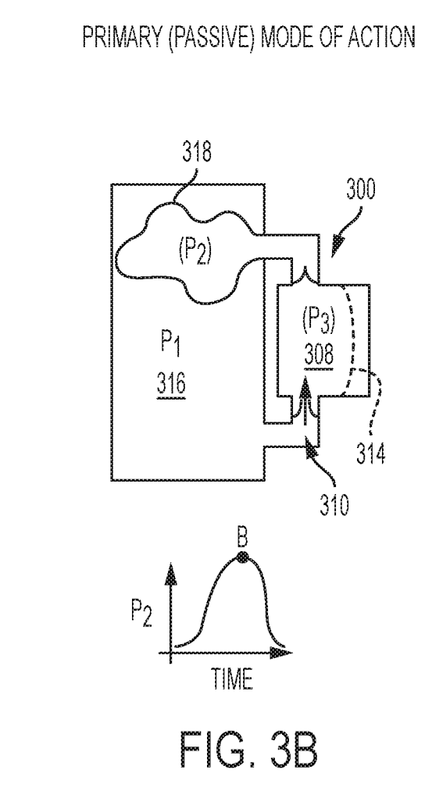
Figure 3C:
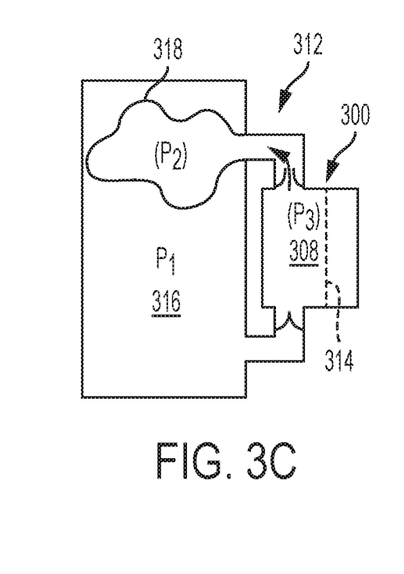

FIGS. 3A-3B are schematic illustrations to help explain the implantable, body-driven shunt pump according to some embodiments of the current invention in operation. FIGS. 3A-3C include an implantable, body-driven shunt pump 300 according to an embodiment of the current invention. The implantable, body-driven shunt pump 300 can be the same as, or similar to implantable, body-driven shunt pump 100 or 200, or can be an alternative embodiment. This embodiment has a gas filled chamber as the contractible component 314 with a membrane between it and the fluid chamber 308. In this example the peritoneal cavity 316 has incompressible fluid at pressure $P_1$ and an organ 318 such as the stomach or urinary bladder 318 that contains incompressible fluid at pressure $P_2$. The pressures $P_1$ and $P_2$ generally stay close to equal to each other, although they can change with time and orientation. Pressure fluctuations of quiet breathing are between 3 and 5 cmH2O, but can reach greater than 50 cmH2O in more aggressive respiratory maneuvers such as a cough or sneeze. These same high pressures can be reached voluntarily by contracting the abdominal muscles against a closed glottis. Regular pressure fluctuations also occur during normal movement such as walking. The implantable, body-driven shunt pump 300 is driven by these changes over time of the pressures $P_1=P_2$.

In FIG. 3A, the implantable, body-driven shunt pump 300 is connected by fluid inlet 304 to the peritoneal cavity 316 and fluid outlet 306 to the organ 318. The pressure $P_3$ of the fluid chamber 308 of the implantable, body-driven shunt pump 300 is essentially the same as $P_1$. In FIG. 3B, $P_1=P_2$ has increased due to bodily functions such as breathing, coughing, sneezing or some other bodily function. At that instant of time, $P_1=P_2$ is greater than $P_3$, which cause the inlet valve 310 to open since it is a one-way valve that opens to allow inflow, but does not allow outflow. After the inlet valve 310 opens, $P_3$ becomes nearly equal to $P_1$ because it is in fluid communication with $P_1$, so the pressure is transferred to the compressible chamber. Because the pressure increases, the volume of the compressible chamber decreases, allowing fluid to flow into the fluid compartment 308. This acts to equilibrate the pressure $P_3$ with $P_1$ and $P_2$ if the increased pressure at the instant of FIG. 3B were maintained. However, the increases of pressure due to breathing, a cough, sneezing, etc. are temporary and the pressure then decreases again, as is indicated in FIG. 3C. This results in the pressures $P_1=P_2$ being less than $P_3$ at that instant, which causes the outlet valve 312 to open so that all three compartment pressures will again act to equilibrate. Then $P_3$ decreases as well because it is in fluid communication with $P_1$. As $P_3$ decreases, the volume of the compressible chamber 314 increases, pushing fluid out of the fluid chamber into the organ 318 through the output valve 312. Valve 310 remains closed because it functions to allow fluid to flow in and not out. In addition, the contractible component 314 can be thought of as a spring mechanism that stores energy when it is compressed and releases energy to drive fluid out of fluid chamber 308 into organ 318. In this way, the implantable, body-driven shunt pump 300 utilizes energy from the changes in pressures $P_1$ and $P_2$ as the source of power to pump fluid from peritoneal cavity 316 into organ 318.

EXAMPLES

Figure 4:
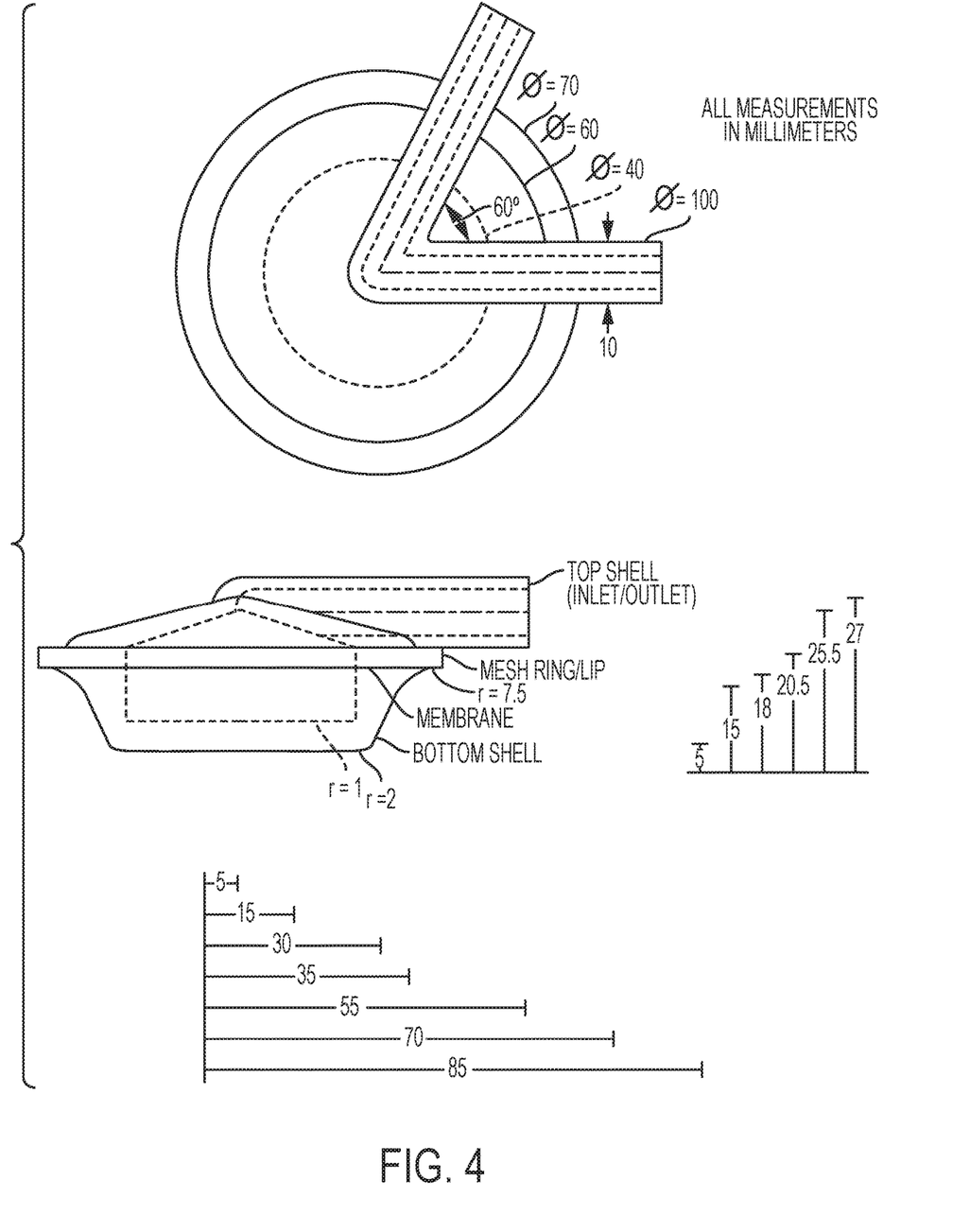
FIG. 4 shows a particular embodiment of an implantable, body-driven shunt pump according to an embodiment of the current invention.

FIG. 4 shows a particular embodiment of an implantable, body-driven shunt pump according to an embodiment of the current invention. Dimensions of the device are shown for that particular embodiment, but the invention is not limited to that particular embodiment and those particular dimensions. The embodiment of FIG. 4 also includes a mesh suture ring attached to and surrounding the portion of the pump body that defines the fluid chamber to facilitate securing the implantable, body-driven shunt pump to subcutaneous tissue.

Some embodiments of the current invention are directed to modular manufacture of the implantable, body-driven shunt pumps. For example, any component of the pump design can be modified (eg, volume of compressible chamber, size/shape of the pump etc) to tailor it to the desired efficacy and patient needs.

Figure 5:
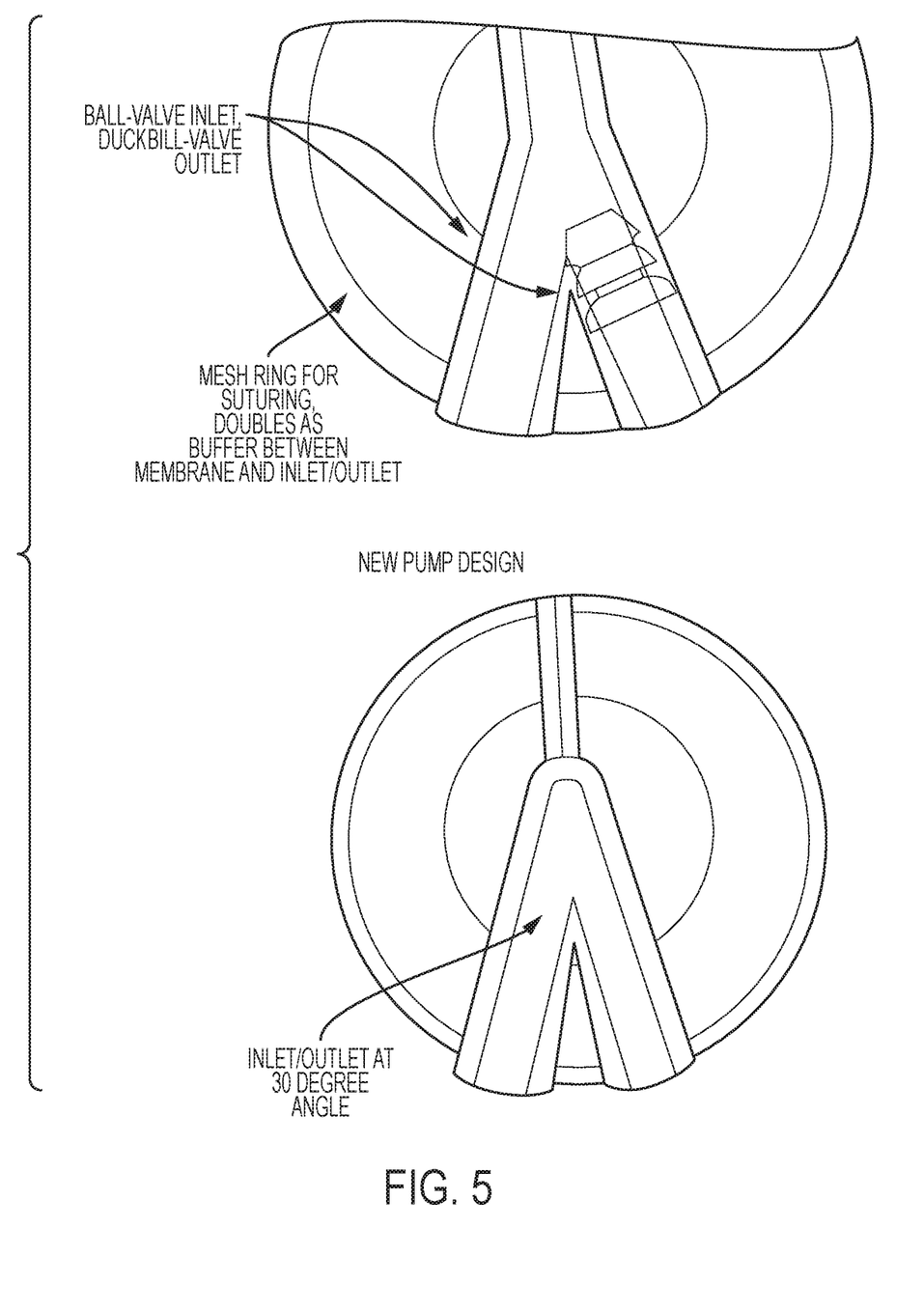
FIGS. 5 and 6 show examples of implantable, body-driven shunt pumps according to additional embodiments of the current invention.
Figure 6:
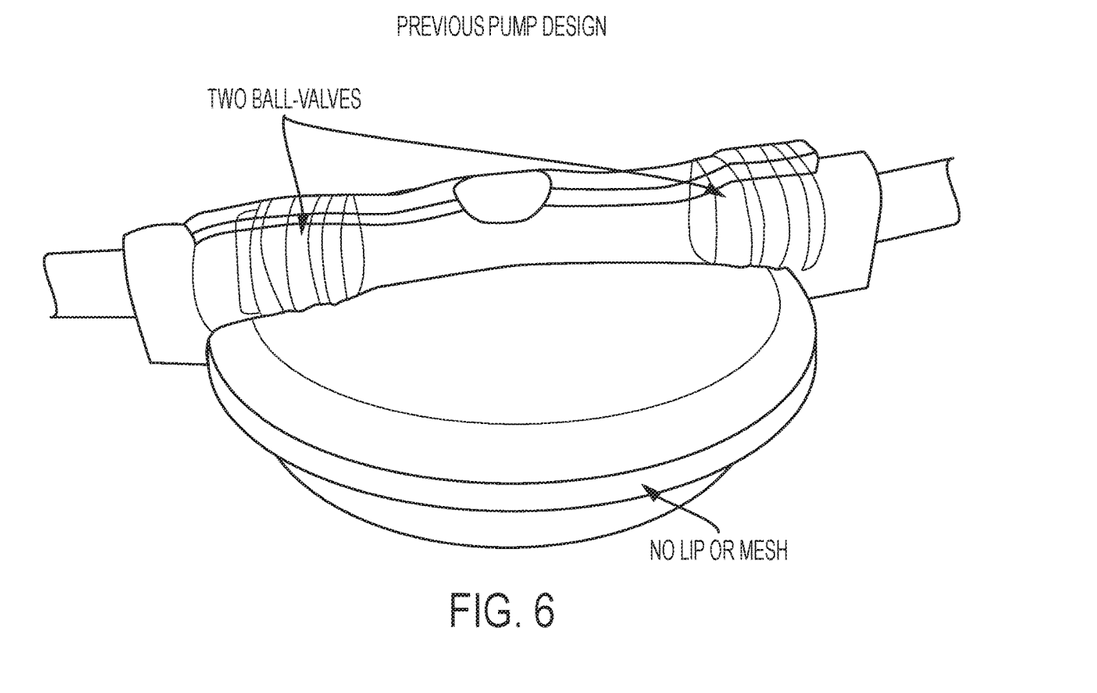

FIGS. 5 and 6 shows some additional examples of implantable, body-driven shunt pump according to some embodiments of the current invention.

Figure 7:
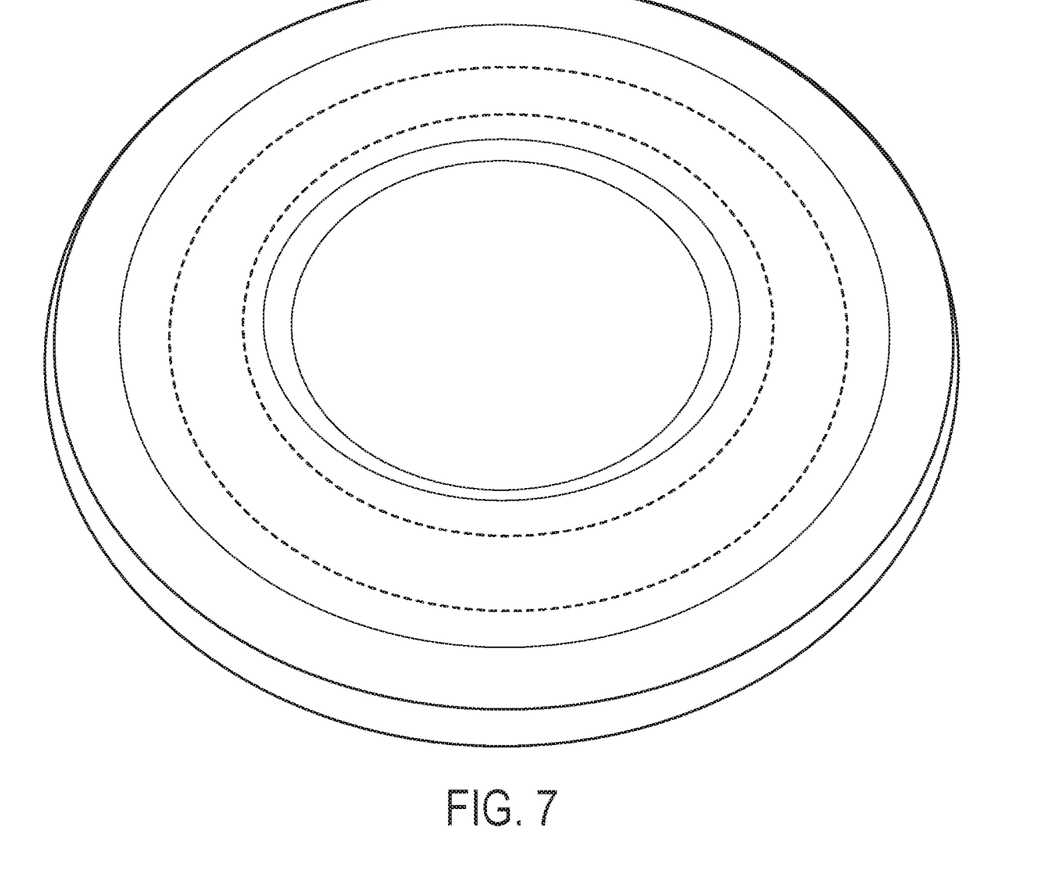
FIGS. 7, 8A-8C, 9A-9F, 10A-10C help explain the production of implantable, body-driven shunt pumps according to some embodiments of the current invention.
Figure 8A:
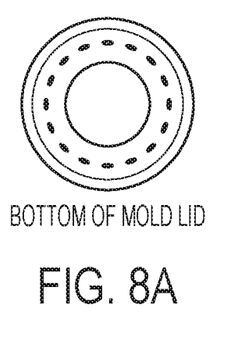
Figure 8B:
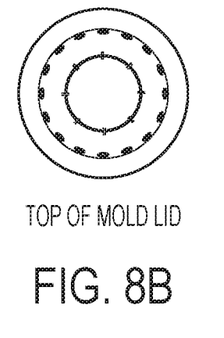
Figure 8C:
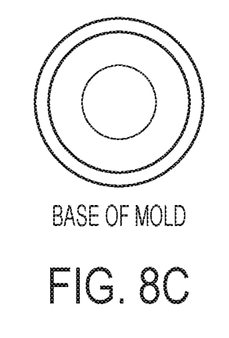
Figure 9A:
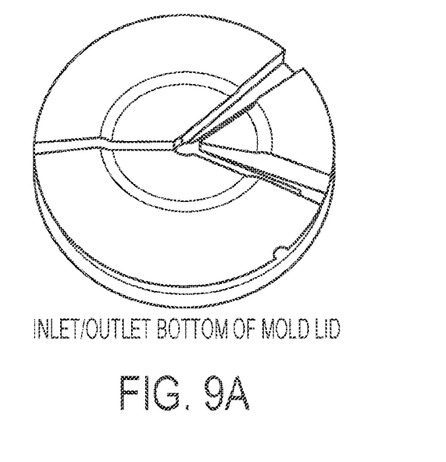
Figure 9B:
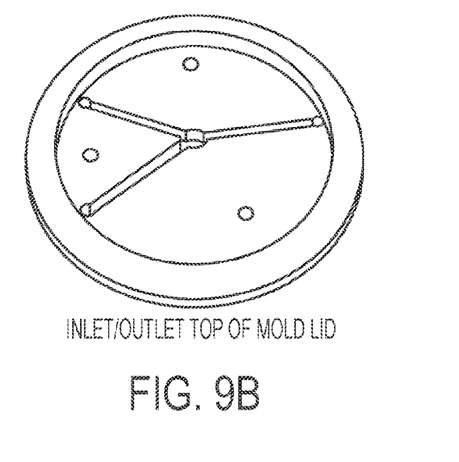
Figure 9C:
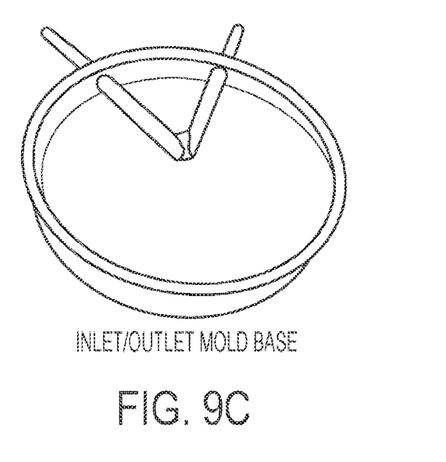
Figure 9D:
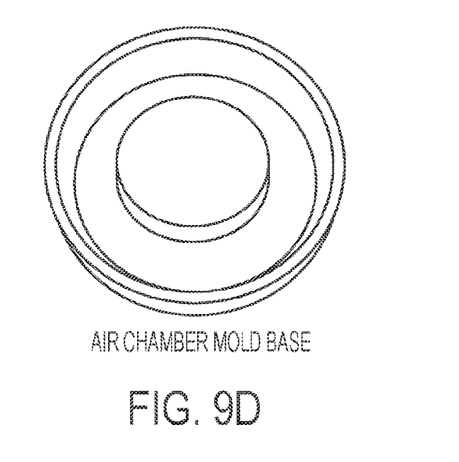
Figure 9E:
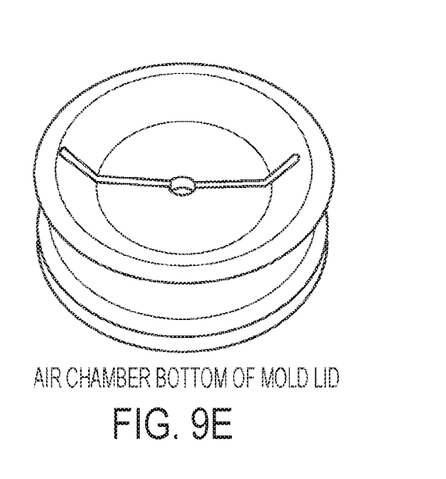
Figure 9F:
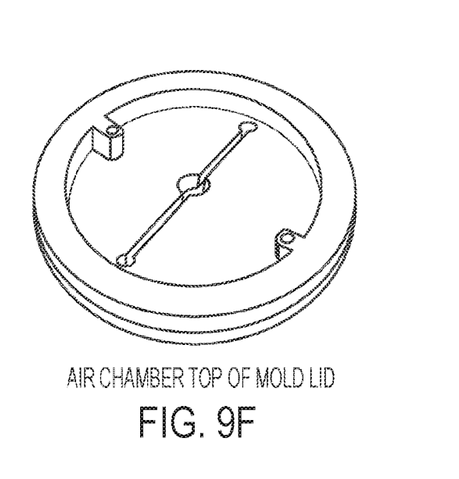

Sewing Mesh for Suture Ring (FIG. 7):
1. Cut two 10×8 cm rectangles out of first aid rolled gauze.
2. Place one rectangle on top of the other so that the overlap forms an 8 cm square with perpendicular stitches.
3. Place two square 7.6 cm Post-It Notes on top and bottom of mesh.
    a. This helps sewing machine grip the work without stretching or deforming mesh
4. Draw four concentric circles on top sticky note with diameters of 4, 4.4, 6.6, and 7 cm.
5. Sew the 4.4 and 6.6 cm diameter circles using Viking Sapphire 930 sewing machine, setting A: woven light with 2.00 stitch length, 0.0 stitch width.
6. Cut around 4 and 7 cm diameter circles so that mesh ring remains.
7. Remove sticky note material by gently ripping around stitches.

Casting Parts for Pump (FIGS. 8A-8C and 9A-9F):
1. Mix 66 g of Sylgard 184 (60 g base, 6 g curing agent)
2. Place ¼" aluminum rods in inlet/outlet mold base, securing with clay at intersection of rods. Secure intersection of rods and mold on outside of mold with clay to prevent leaking.
3. Coat all molds in 3 thin layers of mold release
4. Pour appropriate amount of silicone into base of molds for inlet/outlet and air chamber pump halves.
5. Mesh ring:
    a. Pour thin layer of silicone around inner rim of base of mold, where the gauze will go.
    b. Place gauze on top of silicone, and massage silicone into gauze with gloved hands.
    c. Pour silicone on top of gauze ring, going around the outer rim of the gauze and allowing silicone to flow inward.
    d. Place lid on base mold, and gently push into silicone until mold is closed. Secure with rubber band.
6. Place closed mesh ring mold and open inlet/outlet and air chamber molds in vacuum for 5 minutes.
7. Remove inlet/outlet and air chamber molds from vacuum.
8. Place lids on inlet/outlet and air chamber molds without pushing them in.
9. Place all molds in vacuum for 15 minutes.
10. Remove all molds from vacuum.
11. Gently and uniformly push lids of inlet/outlet and air chamber molds into base, and secure each with a rubber band.
12. Place all molds in oven at 80 degrees Celsius.
    a. Remove mesh ring mold from oven after 9 minutes
    b. Remove inlet/outlet and air chamber mold after 12 minutes
13. Let all molds sit for 12 hours until partially cured.

Spin-Coating Silicone Membrane
1. Mix ~10 g Sylgard 184 at desired base to curing agent ratio (10:1 or 20:1 work best).
2. Place silicone wafer on spin coating machine.
3. Set machine to desired RPM, acceleration, and time.
4. Remove wafer from machine and place in oven at 80 degrees Celsius for 7 minutes or until cured.
5. Gently peel cured membrane from wafer.

Figure 10A:
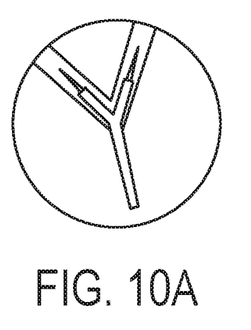
Figure 10B:
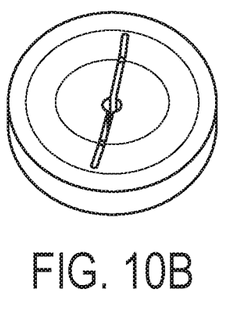
Figure 10C:
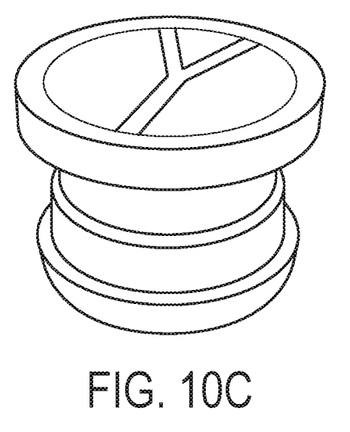

Assembling Pump
1. Mix small amount of Sylgard 184 (5 to 10 grams should be plenty) at a base to curing agent ratio of 2:1².
2. Remove bottoms of inlet/outlet and air chamber molds, and completely remove mesh ring from mold. The silicone should be tacky and soft while still holding its shape.
3. Connect mesh ring to inlet/outlet half of pump:
   a. Position inlet/outlet half of pump so that the lid of the mold is resting flat and the base of the pump half is upwards. (See FIG. 10A.)
   b. Paint the flat surface of inlet/outlet half with thin layer of 2:1 silicone.
   c. Carefully place mesh ring so that it is centered on inlet/outlet half.
   d. Wipe off excess silicone at inner rim of the mesh ring to prevent membrane from getting stuck to inlet/outlet half later on.
4. Connect membrane to air chamber:
   a. Position air chamber half of pump so that the lid of the mold is resting flat and the base of the pump half is upwards. (See FIG. 10B.)
   b. Place membrane over air chamber so that it lies flat, forming a bubble. The air chamber should be tacky enough that the membrane sticks to it a little.
   c. Trim membrane so that it extends only 2 or 3 millimeters into base of air chamber half.
      i. This is done because the silicone only bonds to itself when partially cured. Since the membranes are nearly impossible to work with when partially cured, they are attached fully cured. This means that if the membrane completely covers the air chamber base, the air chamber will not bond to the mesh ring, and the pump may fall apart when subjected to shear stresses.
5. Connect membrane and air chamber to mesh ring and inlet/outlet:
   a. Position air chamber half of pump so that the lid of the mold is resting flat and the base of the pump half is upwards
   b. Paint the flat surface of air chamber half with thin layer of 2:1 silicone, including the overlap of membrane with air chamber but being careful not to disrupt the membrane.
   c. Flip inlet/outlet and mesh ring so that mesh ring is on the bottom, and
      carefully place on air chamber half, making sure it is relatively centered.
         i. If step 3 is done before step 4, mesh ring should have started bonding to inlet/outlet during step 4 and thus should not slip or fall off during this step.
   d. Center the assembly. (See FIG. 10C.)
6. Let assembled pump dry for 12 to 24 hours depending on room temperature.
7. Once pump is cured (silicone on edges is no longer wet or tacky), remove molds.
8. Trim excess silicone from pump.

Figure 11A:
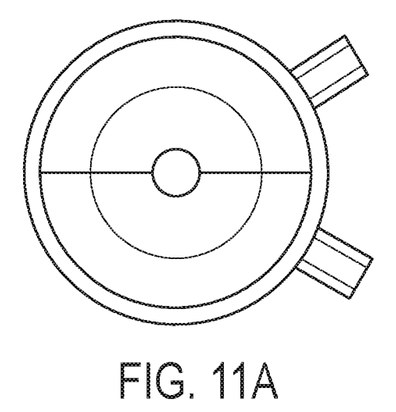
FIGS. 11A-11C show several views of an example of an implantable, body-driven shunt pumps according to another embodiment of the current invention.
Figure 11B:
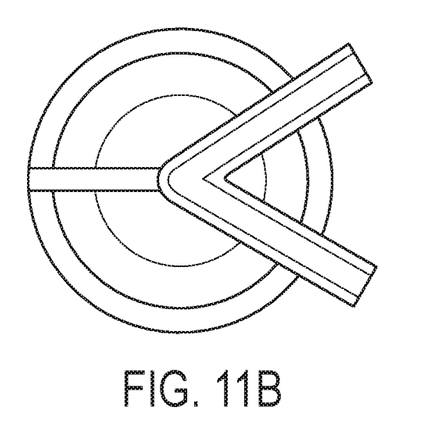
Figure 11C:
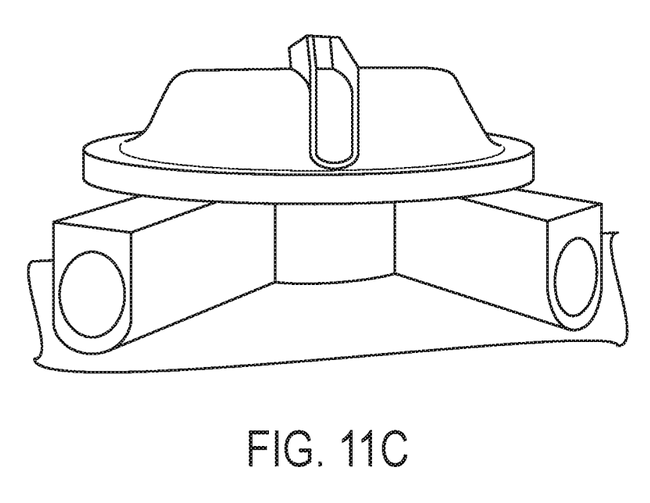

FIGS. 11A-11C show several views of an example of an implantable, body-driven shunt pump according to an embodiment of the current invention.

REFERENCES

1. Salerno et al. Refractory ascites: pathogenesis, definition and therapy of a severe complication in patients with cirrhosis. Liver Int (2010) vol. 30 (7) pp. 937-47
2. Organ Procurement and Transplantation Network: http://optn.transplant.hrsa.gov/
3. White, M. A., Agle, S. C., Padia, R. K., & Zervos, E. E. (2011). Denver peritoneovenous shunts for the management of malignant ascites: a review of the literature in the post LeVeen Era. The American Surgeon, 77(8), 1070-1075.
4. Rössle and Gerbes. TIPS for the treatment of refractory ascites, hepatorenal syndrome and hepatic hydrothorax: a critical update. Gut (2010) vol. 59 (7) pp. 988-1000
5. Saab, S., Nieto, J. M., Lewis, S. K., & Runyon, B. A. (1996). TIPS versus paracentesis for cirrhotic patients with refractory ascites. (S. Saab, Ed.). Chichester, UK: John Wiley & Sons, Ltd.
6. De Waele et al. Intra-abdominal Hypertension and Abdominal Compartment Syndrome. Am J Kidney Dis (2011) vol. 5'7 (1) pp. 159-69
7. http://www.worldgastroenterology.org/assets/downloads/en/pdf/guidelines/14_management_ascites_en.pdf
8. Sort P. et al. Effect of IV Albumin on Renal Impairment and Mortality in Patients with Cirrhosis and SBP. NEJM 1999; 341(6): 403-9.
9. Ginès P et al. Paracentesis with intravenous infusion of albumin as compared with peritoneovenous shunting in cirrhosis with refractory ascites. N Engl J Med. 1991; 325(12):829
10. Fleming K, Aithal G P, Solaymani-Dodaran M, Card T R, West J. Incidence of cirrhosis in the UK: a population-based study. Conference abstract, British Association for the study of Liver Disease, ASM, 2007

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An implantable, body-driven shunt pump, comprising:
   a pump body comprising a fluid inlet, a fluid outlet and a fluid chamber therebetween;
   an inlet valve arranged in said fluid inlet, said inlet valve being a one-way valve arranged such that it is operable to allow fluid flow into said fluid chamber and to prevent fluid flow out of said fluid chamber; and
   an outlet valve arranged in said fluid outlet, said outlet valve being a one-way valve arranged such that it is operable to allow fluid flow out of said fluid chamber and to prevent fluid flow into said fluid chamber,
   wherein said pump body comprises an expandable and contractible component that changes the volume of the fluid chamber in response to a change in pressure of fluid in said fluid chamber.

2. The implantable, body-driven shunt pump according to claim 1, wherein said pump body, said inlet valve, and said outlet valve are all biocompatible materials.

3. The implantable, body-driven shunt pump according to claim 1, wherein said implantable, body-driven shunt pump has a size suitable to be implantable into an abdominal cavity of a patient.

4. The implantable, body-driven shunt pump according to claim 3, wherein said fluid inlet is configured to be arranged in a peritoneal cavity of said patient, and
   wherein said fluid outlet is configured to be arranged in at least one of a stomach or a urinary bladder of said patient while said fluid inlet is arranged in said peritoneal cavity so as to pump fluid from said peritoneal cavity into said stomach or said urinary bladder in response to changes in volume of said fluid chamber.

5. The implantable, body-driven shunt pump according to claim 1, wherein said pump body further comprises an insert of a compressible material as part of a section thereof defining said fluid chamber.

6. The implantable, body-driven shunt pump according to claim 1, wherein said pump body further defines a compressible compartment as part of a section thereof defining said fluid chamber.

7. The implantable, body-driven shunt pump according to claim 6, wherein said compressible compartment comprises a flexible membrane arranged to be in fluid contact with fluid in said fluid chamber during use.

8. The implantable, body-driven shunt pump according to claim 7, wherein said shunt pump further comprises a compressible fluid contained within said compressible compartment.

9. The implantable, body-driven shunt pump according to claim 8, wherein said compressible fluid is a gas having a preselected composition and pressure prior to use.

10. The implantable, body-driven shunt pump according to claim 1, wherein said pump body has a substantially rigid outer surface in a section defining said fluid chamber.

11. The implantable, body-driven shunt pump according to claim 1, wherein said fluid inlet comprises an inlet tube; and wherein said fluid outlet comprises an outlet tube.

12. The implantable, body-driven shunt pump according to claim 11, wherein said at least one of said inlet tube or said outlet tube defines a plurality of holes along a portion of an axial length thereof.

13. The implantable, body-driven shunt pump according to claim 11, wherein said at least one of said inlet tube and said outlet tube is coated with an antibacterial agent.

14. The implantable, body-driven shunt pump according to claim 11, wherein said at least one of said inlet tube and said outlet tube is coated with an anti-coagulant.

15. The implantable, body-driven shunt pump according to claim 1, wherein said pump body comprises silicone.

16. The implantable, body-driven shunt pump according to claim 15, wherein silicone of said pump body is formed with a silicone base to curing ratio of between 5:1 to 100:1.

17. The implantable, body-driven shunt pump according to claim 15, further comprising a mesh suture ring attached to and surrounding a portion of said pump body comprising silicone and defining said fluid chamber to facilitate securing said implantable, body-driven shunt pump to subcutaneous tissue.

18. The implantable, body-driven shunt pump according to claim 1, further comprising a mesh suture ring attached to and surrounding a portion of said pump body defining said fluid chamber to facilitate securing said implantable, body-driven shunt pump to subcutaneous tissue.

19. An implantable, body-driven shunt pump, comprising:
   a pump body defining a fluid inlet, a fluid outlet and a fluid chamber therebetween;
   an inlet valve arranged in said fluid inlet, said inlet valve being a one-way valve arranged such that it is operable to allow fluid flow into said fluid chamber and to prevent fluid flow out of said fluid chamber; and
   an outlet valve arranged in said fluid outlet, said outlet valve being a one-way valve arranged such that it is operable to allow fluid flow out of said fluid chamber and to prevent fluid flow into said fluid chamber,
   wherein said pump body comprises a plurality of expandable and contractible components that change the volume of the fluid chamber in response to a change in pressure of fluid in said fluid chamber,
wherein said pump body has a substantially rigid outer surface in a section defining said fluid chamber, wherein the substantially rigid outer surface in the section defining said fluid chamber pump body comprises silicone.

* * * * *